United States Patent [19]
McQuigg et al.

[11] Patent Number: 5,147,954
[45] Date of Patent: Sep. 15, 1992

[54] 4-(N-BENZYL-N-METHYLAMINO)PYRIDINE ACID SALTS AND USE IN PREPARATION OF POLYMER-SUPPORTED CATALYSTS

[75] Inventors: Donald W. McQuigg; Edward E. Sowers, both of Mooresville; Gerald L. Goe, Greenwood; Eric F. V. Scriven, Greenwood; James G. Keay, Indianapolis, all of Ind.

[73] Assignee: Reilly Industries Inc., Indianapolis, Ind.

[21] Appl. No.: 609,393

[22] Filed: Nov. 5, 1990

Related U.S. Application Data

[60] Division of Ser. No. 352,980, May 17, 1989, Pat. No. 4,968,806, which is a continuation-in-part of Ser. No. 247,152, Sep. 21, 1988, abandoned.

[51] Int. Cl.$^5$ .............................................. C08F 26/06
[52] U.S. Cl. ................................................... 526/265
[58] Field of Search ........................................ 526/265

[56] References Cited

PUBLICATIONS

Menger, F. M., McCann, D. J., *J. Org. Chem.* 50 3928 (1985).
10th Intl. Conf. Heterocycl Chem. (1985).
Tomoi, M., Goto M., Kakiuchi, H. J., *Polym. Sc., Polym. Chem.*, 25 77 (1987).
Storck, W., Manecke, G. J. Mol. Cat., 30 145 (1985).
Koning, C. E., Eshuis, J. J. W., Viersen, F. J., Challa, G., *Reactive Polym.* 4 293 (1986).
Shinkai, S., Tsuji, H., Hara, Y., Manabe, O., *Bull. Chem. Soc. Jpn.*, 54 631 (1981).
Tomoi, M., Akada, Y., Kachiuchi, H. *Macromol. Chem., Rapid Commun.*, 3 537 (1982).
Deratani, A., Darling, G. D., Horak, D., Fréchet, J. M. J., *Macromolecules,* 20 767 (1987).
Deratani, A., Darling, G. D., Fréchet, J. M. J., *Polymer* 28, 825–830 (1987).
Hierl, M. A., Gamson, E. P., Klotz, I. M., *J. Am. Chem. Soc.,* 101 6020 (1979).
Delaney, E. J., Wood, L. E., Klotz, *J. Am. Chem. Soc.* 104 799 (1982).
Klotz, I. M., Massil, S. E., Wood, L. E., *J. Polymer Sc., Polymer Chem. Ed.,* 23 575 (1985).
Guendouz, F. Jacquier, R., Verducci, J. *Tetrahedron Lett.* 25 4521 (1984).
Hofle, G., Steglich, W., Vorbruggen, H., *Angew. Chem. Int. Ed. Engl.,* 17, 569 (1978).
Scriven, E. F. V., *Chem. Soc. Rev.* vol. 12 No. 2 (1983).
Frechet, J. M. J., Deratani, A., Darling G., Lecavalier, P, Li, N. H., Macromol. Chem. Macromol Symp., 1, 91 (1986).
Patchornik, A., *Chemtech,* Jan., 1987, 58.

*Primary Examiner*—Joseph L. Schofer
*Assistant Examiner*—Alex H. Walker
*Attorney, Agent, or Firm*—Woodard, Emhardt, Naughton, Moriarty & McNett

[57] ABSTRACT

A cross-linked polymer-supported 4-(N-benzyl-N-methylamino) pyridine material and process for its preparation in high yield and having effective physical and catalytic properties. The polymer-supported catalyst is characterized by the suspension copolymerization of an organic phase containing the corresponding vinyl-substituted pyridine monomer, a styrene monomer, and a suitable cross-linking agent and free radical-generating catalyst in the presence of an aqueous phase containing a cellulose ether derivative as the stabilizing agent. A purified acid salt of the vinyl-substituted pyridine monomer useful in polymerizations and stable for storage as either a solid or an aqueous solution.

20 Claims, No Drawings

4-(N-BENZYL-N-METHYLAMINO)PYRIDINE ACID SALTS AND USE IN PREPARATION OF POLYMER-SUPPORTED CATALYSTS

CROSS-REFERENCE

This application is a division of application Ser. No. 352,980 filed May 17, 1989, now U.S. Pat. No. 4,968,806 which is a continuation-in-part of U.S. patent application Ser. No. 277,152 filed Sep. 21, 1988, now abandoned.

BACKGROUND OF THE INVENTION

This invention relates generally to polymer-supported catalysts having pyridylamino functionality, and in particular to a cross-linked copolymer of vinyl-substituted 4-(N-benzyl-N-methylamino)pyridine and a styrene monomer derivative characterized by improved physical properties and marked catalytic activity, and further to an improved acid salt form of the 4-(N-benzyl-N-methylamino)pyridine monomer and the use of the same for preparing polymer-supported catalysts.

By way of general background, it has been recognized for some time that 4-dimethylaminopyridine (commonly referred to as "DMAP") and certain of its dialkylamino analogs are highly effective catalysts for acylations, alkylations and other related reactions. Hofle, G., Steglich, W., Vorbruggen, H., *Angew. Chem. Int. Ed. Engl.*, 17, 569 (1978); Scriven, E. F. V., *Chem. Soc. Rev.*, 129 (1983). Also recognized for some time has been the desirability of a polymer-bound or supported version of such DMAP-like catalysts in view of the potential advantages of ease of recovery and repeated use along with the adaptability of such catalysts in both static and flow systems. Although such polymers could be soluble, it is understood that insoluble, heterogeneous gel or macroreticular resin beads provide the greater advantages in ease of removal and recyclability. Fréchet, J. M. J., Deratani, A., Darling, G, Lecavalier, P., Li, N. H., *Macromol. Chem. Macromol. Symp.*, 1 91 (1986); Patchornik, A., *Chemtech*, January, 1987, 58.

Accordingly, much investigation has taken place in search of an effective polymer-supported DMAP-like catalyst. For example, Klotz and his coworkers were the first to report such a polymer made by attaching an acid-functionalized dialkylaminopyridine to a polyethyleneimine polymer. Hierl, M. A., Gamson, E. P., Klotz, I. M., J. Am. Chem. Soc.. 101. 6020 (1979). Klotz in combination with others subsequently reported similar functionalized polyimines, and demonstrated their catalytic ability by kinetic experiments on the hydrolysis of p-nitrophenyl caproate. Delaney, E. J., Wood, L. E., Klotz, I. M., *J. Am. Chem. Soc.*, 104. 799 (1982); Klotz, I. M., Massil, S. E., Wood, L. E., *J. Polymer Sc., Polymer Chem. Ed.*, 23, 575 (1985). These polymers suffered, however, from the drawback that the pyridine was attached to the polymer backbone by an amide linkage which was susceptible to scission as when regenerating the resin using sodium hydroxide in acetylation reactions involving acyl halides.

Verducci and his coworkers reported attaching 4-piperidinylpyridine, among other DMAP-like moieties, to a Merrifield resin also through an amide bond. Guendouz, F., Jacquier, R., Verducci, J., *Tetrahedon Lett.*, 25, 4521 (1984). The amide bond in this polymer, however, was reported to stand up well on recycle in the catalytic acetylation of 1-methylcyclohexanol at 70° C. and 24 hours.

Nevertheless, more popular approaches to achieve DMAP-like polymer catalysts have avoided the use of amide linkages altogether. For example, Shinkai and his coworkers reported attaching 4-chloropyridine to an aminomethylpolystyrene to yield a polymer-supported 4-(N-benzyl-N-methylaminq)pyridine (which functional group has commonly become known as "BMAP"). Shinkai, S., Tsuji, H., Hara, Y., Manabe, O., *Bull. Chem. Soc. Jpn.*, 54, 631 (1981). This polymer-bound BMAP material was reported to effectively catalyze simple esterifications, but the product achieved by Shinkai had the disadvantages of including a high percentage of a secondary amine which interfered with the reaction unless alkylated prior to use.

Another group of investigators led by Tomoi has compared two other approaches to achieve a similar polymeric BMAP catalyst. Tomoi, M., Akada, Y., Kakiuchi, H., *Macromol. Chem., Rapid Commun.*, 3, 537 (1982). Tomoi reported, among other things, that a route involving copolymerization of the preformed BMAP monomer gave a better catalyst product. However, more recently a group led by Fréchet challenged this conclusion, reporting that preformed chloromethylated polystyrene can be modified readily and quantitatively to produce an even better catalyst. Fréchet, J. M. J., Deratani, A., Darling, G, Lecavalier, P., Li, N. H., *Macromol. Chem. Macromol. Symp.*, 1, 91 (1986). Menger and his coworkers have also reported success in converting a linear chloromethylpolystyrene resin to the corresponding linear BMAP polymer which has proven effective in well-known DMAP-catalyzed processes such as the conversion of linalool to linalyl acetate which has definite commercial interest. Menger, F. M., McCann, D. J., *J. Org. Chem.* 50, 3928 (1985).

The extent of work in this field has also led groups headed by Fréchet, Tomoi, Manecke and Challa to study the effects of variation of the frequency of BMAP-to-styrene units as well as variations of cross-linking and of the length and nature of the spacer arm or component separating the pyridylamino functional group from the polymer backbone. To this end, numerous polymers have been reported by these groups with varying degrees of detail. Deratani, A., Darling, G. D., Horak, D., Fréchet, J. M. J., *Macromolecules*, 20, 767 (1987); Deratani, A., Darling, G. D., Fréchet, J. M. J., *Polymer* 28, 825-830 (1987); 10th Intl. Conf. Heterocycl. Chem. (1985); Tomoi, M., Goto, M., Kakiuchi, H. J., *Polym. Sc., Polym. Chem.*, 25, 77 (1987); Storck, W., Manecke, G., *J. Mol. Cat.*, 30, 145 (1985); and Koning, C. E., Eshuis, J. J. W., Viersen, F. J., Challa, G., *Reactive Polym.*, 4, 293 (1986).

In reviewing these collective efforts, as highlighted above, it is evident that the paramount interest to date has been to confirm the ability to synthesize polymer-supported catalysts of these types approaching DMAP activity. Accordingly, little or no effort has gone into characterizing in a quantitative or qualitative way the physical or chemical properties of the polymer compounds thus far obtained. Nevertheless, these same properties dictate the ultimate commercial utility of such polymeric catalysts in whatever reactions they are used.

For example, while these considerable scientific publications have demonstrated the general or potential utility of polymeric catalysts of this type, nearly all have done so with polymers having low degrees of cross-linking up to only about 2% by weight of the total polymerizable monomer present. These prior art polymers have been reported and proven to be mechanically weak and to exhibit noticeable breakage and disintegration both as formed and during use, particularly with even moderate attempts at recycling. In addition, these polymers have exhibited substantial swelling in excess of 100–200% by volume upon exposure to a solvent which has aggravated breakage upon recapture. This is a definite disadvantage in many commercial processes, for example, where space constraints are important.

Moreover, these polymers prepared according to the literature references contain significant amounts of granular powders, flake or other irregular shapes instead of the predominant bead form that is preferred. Such unwanted particles are mechanically unstable and suitable for use only in stirred-slurry or other reactors where clogging of filters or lines is not a concern and where recycling of the catalyst is not contemplated. The gel-type bead segments that are present in these reference materials are nonuniform in size or configuration, exhibit great deviation from the average or median size present, and do not show the durable, hard form that is preferred. While Fréchet has reported making a 34% divinylbenzene (DVB) cross-linked macroreticular resin also within this class, he reported and subsequent testing has confirmed that it has inferior chemical and physical properties as a catalyst in the acylation of 1-methylcyclohexanol. In addition, Fréchet's resin made from his preferred chloromethylated polystyrene process may contain quaternary salt from unwanted side reactions which can react to ring-open under strongly basic conditions as often encountered.

Therefore, while certain publications have reported the synthesis of polymer-supported DMAP-like resins and their general catalytic ability, there has been and remains today the need for a catalyst of this type in both gel and macroreticular form that exhibits overall mechanical stability as expected with higher degrees of cross-linking while retaining effective chemical properties believed lost in such materials. Improved physical properties of surface texture and configuration, uniformity and durability are also desired, as are chemical properties approaching the catalytic potency and universal acceptance of DMAP and its analogs.

Further, difficulties in handling the BMAP monomer starting material have been encountered. In particular, BMAP monomer in its free base form is quite reactive. As a monomer related to styrene, BMAP monomer tends to polymerize readily and does not survive manipulations well. For example, even distillation in a falling film still under high vacuum produces very low recovery of BMAP monomer free base. Purification by crystallization is also difficult as BMAP monomer free base is a low melting solid. Consequently, present preparations of polymer-supported 4-(N-benzyl-N-methylamino)pyridine catalysts employ relatively impure BMAP monomer.

In synthesizing the free base, the BMAP monomer according to the references above is generally isolated as a solution of a crude product which may contain a number of useless, even interfering, by-products. Among these may be mineral oil, unreacted vinylbenzyl chloride and 4-methylaminopyridine (MAP). Additional unknown compounds and intractable materials are also present. The presence of these by-products in the BMAP monomer starting material, and the previous inability to effectively purify it, have detracted from the purity of the catalyst product and resultantly from its efficient and effective use.

Also, the polymerizations themselves have been required to be carried out relatively quickly after synthesis of the BMAP monomer due to its reactivity and inherent instability. As a result, preparation of the monomer has been limited to the quantity needed for immediate use as the free base cannot be stored for any appreciable length of time pending further use. Preparation of quantities of monomer exceeding amounts immediately consumable have typically resulted in loss of this excess and waste of the materials.

SUMMARY OF THE INVENTION

The applicants' present invention addresses these needs in the discovery of a cross-linked polymer-supported 4(N-benzyl-N-methylamino)pyridine material of superior physical properties and high activity and effectiveness as a catalyst for acylation, alkylation and other related reactions. This polymeric BMAP catalyst is prepared through the free radical suspension copolymerization of an organic phase comprising the vinyl-substituted BMAP monomer free base, a styrene monomer and a suitable free radical-generating catalyst and cross-linking agent in the presence of a selected aqueous suspending medium. Further, an acid salt form of the BMAP monomer has been discovered which is stable as a solid or in solution and is easily neutralized to the free base for use in the suspension copolymerization process.

In its preferred form, the Applicants' polymer-supported BMAP material is characterized by its generally spherical and smooth bead form and substantially uniform size ranging up to about 1.0 mm in diameter and exhibiting minimal deviation from the median or average bead size in a given batch. The beads are hard and durable, being both easily recoverable following copolymerization and readily recyclable in use. The beads may have a gel or a macroreticular structure, as desired, depending upon the degree of cross-linking and other factors such as the presence of a suitable diluent such as an organic solvent in the copolymerization process. The beads are also characterized by the absence of any significant amount of granular powders, flake or other irregular particles either as originally formed or as the result of unwanted deterioration from normal catalytic use. The beads have further shown to have highly effective catalytic activity approaching that of DMAP in the reactions tested.

Further, this preferred polymer-supported BMAP material is characterized by its suspension copolymerization process and, in particular, by the use of an aqueous phase comprising a cellulose ether derivative as the stabilizing or suspending agent. With this preferred suspension component, high percentages of the desired polymer beads have been recovered in excess of 90% by weight of the total product which exhibit the surprisingly superior physical properties of shape, size, hardness and overall quality and appearance described herein while also demonstrating unexpected and effective catalytic utility also described.

Still further, the BMAP monomer containing the amino functionality has been discovered to form a stable salt with a relatively strong acid such as hydrochloric acid, sulphuric acid, hydrobromic acid and the like. Surprisingly, these acid salts of the BMAP monomer are stable as solid amine salts. More surprisingly, these BMAP acid salts are also relatively stable in an aqueous solution of the parent acid. Moreover, these acid salts can be stored for extended periods pending later use, and particularly use in the Applicants' same suspension copolymerization process where the salt is either neutralized in situ immediately prior to the polymerization reaction or is neutralized and then isolated immediately before use. Also, these BMAP acid salts used in this manner may be stored either as the solid form or as an aqueous solution of the parent mineral acid.

One advantage of the present invention is accordingly the economic preparation of the BMAP monomer in quantities which may be larger than immediately needed. Surplus BMAP monomer ma be converted to one of the acid salts of the present invention and stored for future use.

A second advantage of the present invention is that the BMAP monomer free base is purified by isolation as an acid salt according to the Applicants' discovery, which salt is then substantially free from the impurities found in previous processes. This purified monomer may then be used in the suspension copolymerization process with the resultant polymer being of significantly greater purity than those polymers prepared from unpurified BMAP monomer.

A further advantage is the convenience of use of the acids salts of the present invention. The salts are easily converted to the BMAP free base by neutralization with a base.

A still further advantage is an improved process for preparing polymer-supported 4-(N-benzyl-N-methylamino) pyridine catalysts using the BMAP acid salts of the present invention.

Related objects and advantages of the present invention will be apparent from the following description.

DESCRIPTION OF THE PREFERRED EMBODIMENT

For the purposes of promoting an understanding of the principles of the invention, reference will now be made to the several embodiments and specific language will be used to describe the same. It will nevertheless be understood that no limitation of the scope of the invention is thereby intended, such alterations and further modifications in the device, and such further applications of the principles of the invention as illustrated therein being contemplated as would normally occur to one skilled in the art to which the invention relates.

In accordance with the above, the applicants have discovered a commercially significant DMAP-like polymer resin containing 4-methylaminopyridine groups functionally bound to a cross-linked styrene backbone at the 4-amino site through a vinylbenzyl linkage. The preparative process of choice comprises the suspension copolymerization of vinyl-substituted 4-(N-benzyl-N-methylamino)pyridine with a styrene monomer and a suitable cross-linking agent and free radical-generating catalyst. This is contrasted by the indirect method reported in the literature which involves subsequently attaching 4-pyridineamine groups to a preformed chloromethylated polystyrene resin The applicants found that this indirect method incorporated less pyridylamino functional groups onto the preformed polymer, required longer reaction times and resulted in greater likelihood of contamination from quaternary salt formation or residual chloromethyl components. In any case, the preferred polymer resins of the invention have been identified by infrared (I.R.) and elemental combustion analysis and their catalytic activity has been confirmed by reactions such as those reported in Example 4 below involving a Fries ester rearrangement and the acetylation of 1-methylcyclohexanol. In each reaction, the applicants' heterogeneous polymeric catalyst performed effectively and compared favorably with DMAP used under homogeneous conditions.

Referring further to the process embodiment of the invention, the terms "free radical suspension copolymerization" are well known to those skilled in this art and comprise the process of polymerizing a comonomer mixture which has been suspended in the form of droplets in a medium of some composition in which the monomers are at least substantially insoluble. The discrete nature of these droplets and the size and stability of the suspension depend in large part on the nature of the medium used including its individual components or additives, as well as on various physical factors in the procedure such as stirring rate, temperature and the like. The medium used in this invention is an aqueous phase suspension of a particular class of stabilizing agent as described below.

As the copolymerization proceeds, these droplets appear and take on various forms which will affect their physical and chemical properties in later use. Although it is common to refer to all such polymer droplets as "beads," in fact they may range from granular powders, flakes or other irregular-shaped particles such as produced by the prior art processes discussed above to the predominantly uniform and smooth, hard spherical beads achieved by the applicant's invention.

One method of promoting the copolymerization is to provide a suitable catalyst which when elevated to a sufficient temperature will decompose to provide free radicals which function as initiators for the reaction. Two general classes of such free radical-generating catalysts are known, those being peroxides and azo compounds. The selection of an initiator within these groups, and its amount and method of use, is within the knowledge and skill of the art and depends on availability, on the specific comonomer mixture used and on other factors affecting the reaction. The catalyst used in the applicants' work has been an azo compound identified as 2,2'-azobis-(2,4-dimethylvaleronitrile) and marketed by E. I. du Pont de Nemours & Company (DuPont) under the trademark Vazo 52. The preferred range of this catalyst has been from about 0.1–1.0% by weight of the total comonomer components used. It is nonetheless understood that other catalysts within these groups are similarly suited for this purpose and are within the scope of the invention.

As the copolymer of the applicants' invention is an insoluble or heterogeneous material, a suitable cross-linking agent must also be included in the organic component during the copolymerization process. Many such cross-linking agents are commercially available, and their utility and interchangeability in reactions such as the process at hand are well known to those skilled in this art. The applicants have to date used a commercial divinylbenzene (commonly referred to as "DVB") for this purpose in amounts varying according to the desired physical structure of the reaction product as further discussed below. In any case, however, it is understood that other suitable cross-linking agents are known to exist and are within the scope of the invention.

The reaction conditions for the preferred process such as the temperatures and times for the copolymerization to occur as well as appropriate equipment and procedures such as the desirability of agitation and the like are also well known to those practiced in this art.

Accordingly, the same require little further elaboration in this specification. For example, it is known that the temperature to initiate polymerization depends as a practical limit on the decomposition temperature of the free radical-generating catalyst used. As some reactions in this class are exothermic, little or no additional heating is necessary although some may be desirable at later stages to assure complete copolymerization of the monomer present. For the applicants' preferred Vazo 52 catalyst, an initiation temperature of about 55° C. was employed with an elevated temperature of about 85° C. used to finish off the reaction. With other suitable catalysts, this initiation temperature may increase or decrease significantly coupled with completing the reaction at temperatures up to or at reflux of about 100° C. or above. It is similarly known, for example, that oxygen inhibits these reactions and was therefore kept from the system in the Examples below by maintaining a nitrogen purge during the copolymerization process.

Referring now to a second embodiment, the cross-linked polymer-supported BMAP material in accordance with the invention is characterized by being suspension copolymerized in the presence of a particular aqueous phase which comprises a cellulose ether derivative as the stabilizing or suspending agent. Suitable cellulose ether derivatives (and examples of their available commercial trademarks and sources) include methylcellulose (such as Methocel A from Dow Chemical Corporation of Midland, Mich. and Culminal from Aqualon Company of Wilmington, Del.); hydroxyethylcellulose (such as Natrosol 250 from Aqualon and Cellosize from Union Carbide Corporation of Danbury, Conn.); hydroxypropylcellulose (such as Klucel J from Aqualon); hydroxypropyl methylcellulose (such as Methocel E, F, J and K and 50-123 from Dow Chemical and Culminal MHPC from Aqualon); hydroxyethyl methylcellulose (such as Culminal from Aqualon); carboxymethyl methylcellulose (such as CMMC from Aqualon); hydrophobically-modified hydroxyethylcellulose (such as HMHEC WSP-M 1017 from Aqualon); carboxymethyl hydroxyethylcellulose (such as CMHEC 37L from Aqualon); and hydroxypropyl hydroxyethylcellulose (such as Natrovis from Aqualon). In many cases, these trademarks represent classes or series of compounds offered by these companies which will work effectively in the present process. Moreover, this listing of cellulose ether derivatives is not exhaustive as there are other such derivatives both naturally-occurring and synthetic which are also suited for this purpose and are within the scope of the invention.

The amount required of this stabilizing additive in the aqueous phase to effect the desired copolymerization of the present invention will vary according to the cellulose ether used as well as other factors. From work thus far some preference has been shown for hydroxypropyl methylcellulose (such as Methocel 50-123 from Dow Chemical), hydrophobically-modified hydroxyethylcellulose (such as HMHEC WSP-M 1017 from Aqualon) and carboxymethyl hydroxyethylcellulose (such as CMHEC 37L from Aqualon) in preferred concentrations up to about one-half percent (0.50%) by weight of the total aqueous phase. Most preferred have been concentrations of about one-tenth percent (0.10%) by weight. The limiting factors in selecting these derivatives and amounts are practical ones such as availability and ease of use and process concerns affecting viscosity and the proper maintenance of the suspension once achieved. In any case, the use of these cellulose ether derivatives in the aqueous phase of the present invention has yielded superior copolymer beads having effective physical properties as well as highly active catalytic functionality. These results were unexpected and are a significant improvement over the additives reported in the literature for preparing similar polymer-supported DMAP-like catalysts.

The selection of materials for the organic monomer phase in accordance with the invention involves preparing crude vinyl-substituted 4-(N-benzyl-N-methylamino)pyridine (BMAP) monomer. This preparation may be accomplished, for example, through the reaction of 4-(N-methylamino)pyridine with vinylbenzylchloride as reported in the 1982 Tomoi article previously referenced, although other methods may be available which would likely result in the characteristic vinyl-linkage instability and impurity in the monomer product. Further, the crude BMAP may be prepared well in advance, purified by transformation from the free base to the acid salt form, and stored for later use whereupon it is neutralized, all according to the Applicants' further discovery as described in more detail as the fourth embodiment found below. Also present in the organic phase is a styrene monomer component including styrene itself and/or a substituted styrene derivative such as ethylstyrene, which is similarly suited for this purpose and is within the scope of the invention. Still further, there is a suitable free radical-generating catalyst and cross-linking agent in accordance with the descriptions above.

The concentration and ratio of these monomer materials in the organic phase will vary appreciably depending upon the desired physical and chemical characteristics of the resulting copolymer product. BMAP loading is a convenient measure as the amount of pyridylamino groups present has a direct relationship to the functioning of the copolymer resin as a catalyst in acylation, alkylation or other related reactions. For example, the preferred polymer-supported material has been successfully prepared in accordance with the invention across a wide range of BMAP loading up to about 50% by weight of the BMAP monomer compared to the total monomer present in the organic phase. This is approximately equivalent to a mole percent up to about 33% and to molar ratio up to about 1:2 of BMAP monomer to total styrenic monomer in the organic phase. In this regard, the term "total styrenic monomer" is meant to include styrene and any styrene derivatives such as ethylstyrene and divinylbenzene, and is in deference to the fact that commercial DVB cross-linking agent is a styrene derivative having some unreacted ethylstyrene component. For example, the 55% DVB used in the Examples below typically has about 45% ethylstyrene remaining in the material. This entire DVB component including the extraneous styrenic material is included in the BMAP loading calculation. In a similar manner, the most preferred BMAP loading from work performed to date is about 34% by weight of BMAP monomer compared to total styrenic monomer in the organic phase, which equates to about 20 mole percent and to a molar ratio of about 1:4.

As alluded to earlier, the amount of agent such as divinylbenzene in the organic monomer phase directly affects the degree of cross-linking and to a large extent both the physical and chemical properties of the resulting copolymer catalyst product. With this in mind, decreasing concentrations of DVB below about 8–10% by weight in accordance with the invention has produced effective gel resins that are generally translucent and hard, durable beads in appearance and exhibit increasing swellability and accompanying activity typical of lower degrees of cross-linking. Increasing concentrations of DVB above about 8–10% by weight, on the other hand, has produced similarly effective gel resins that are generally harder bead forms less subject to swelling or disintegration during use and exhibit some possible loss of accompanying activity typical of such higher degrees of cross-linking. By increasing still further the concentration of DVB coupled with the inclusion of a suitable diluent such as an organic solvent in the monomer phase during copolymerization, the resulting product has been effectively changed from a gel to a macroreticular bead form as determined by the presence of a permanent pore structure and opaque appearance typical of such resins upon later removal of the solvent. Although many suitable solvents exist for this purpose, the applicants have employed a VMP Naphtha material distributed by Chem Central of Indianapolis, Ind. in about 33% by weight of the total organic phase. As shown in Example 4 below, the applicants. preferred polymeric material has shown effective catalytic properties at 15% cross-linking in both gel and macroreticular forms. Selection of the appropriate cross-linking and resin form for a given catalytic reaction, including the nature and amount of any solvent used, is well within the knowledge and skill of those practiced in this art and is within the scope of the present invention.

Referring to still a third embodiment, the cross-linked polymer-supported BMAP material of the invention is further characterized and distinguished from the art by the same physical and catalytic properties which have been surprisingly discovered. In particular, the preferred copolymer material has been prepared in high yield well in excess of 90% of the total recovered product. More importantly, the preferred material has shown little or no evidence of clumping or of the presence of granular powders, flake or other irregular material to hamper later use or recycling of the catalyst. On the contrary, the preferred material has exhibited a generally smooth and spherical bead form with the further advantage of a substantially uniform size distribution ranging up to about 1.0 mm in diameter and a minimal deviation from the median or average bead size in a given reaction. Subsequent testing has shown these same preferred copolymer beads resist attrition as a result of swelling in the case of gel resins and overall are hard, highly durable and easily recyclable in both gel and macroreticular forms. These beads have further shown surprisingly effective catalytic activities approaching those of DMAP in reactions tested as highlighted in Example 4 below, but with the added advantages attendant their heterogeneous structure.

As noted above, a fourth embodiment of the present invention involves isolating and purifying the BMAP monomer as an acid salt from the crude vinyl-substituted 4-(N-benzyl-N-methylamino)pyridine monomer reaction solution. As used in this context, the term "acid salt" is meant to include both BMAP acid salt in solution and BMAP acid salt in solid form. After the reaction is complete, the reaction solution contains a number of by-products and unreacted reactants, most of which are incapable of forming a salt. Past attempts in the references to purify the monomer have led to very low recovery of the compound. For example, purification by crystallization is very difficult as the monomer is relatively low melting and usually handled as a liquid. Attempts to purify the monomer by distillation have also met with limited success. Even when a falling film still has been used under high vacuum the monomer yields are quite low.

In contrast to these failed attempts, the Applicants have discovered that the crude BMAP monomer may be readily isolated and purified with an acid sufficiently strong to form an acid salt with the monomer. Surprisingly, these acid salts of the BMAP monomer free base are stable to repeated and normal handling and further are stable to extended storage pending later use. Moreover, subsequent polymerizations using this BMAP monomer, once neutralized, result in as good or better performance of the polymer products along with attendant benefits such as increased purity, reactivity, efficiencies of operation and the like.

One manner of isolating the BMAP monomer as an acid salt is by subjecting the crude BMAP monomer, perhaps dissolved in a solvent substantially insoluble in water such as toluene, to extraction with an aqueous acid such as hydrochloric acid, sulphuric acid, hydrobromic acid or p-toluenesulfonic acid, methanesulfonic acid, formic acid, phosphoric acid or the like, but preferably hydrochloric acid. The extraction may take place while the BMAP monomer is still present in the reaction solvent from its preparation. Addition of the acid in this way results in the formation of two layers, one an organic layer and the other an aqueous layer. The neutral compounds, i.e., impurities, present in solution and incapable of forming a salt remain in the organic layer, while BMAP monomer and minor compounds capable of forming a salt are taken into the aqueous layer. For example, these minor compounds may include methylamino pyridine and comparable side products. The organic layer is then separated from the aqueous layer by decanting or by other methods known to those ordinarily skilled in the art. The resulting separated aqueous solutions containing the BMAP acid salt having a purity greater than 90% may then be stored for later use if so desired, or may be used presently in whole or in part. By way of illustration, the acid salt solution may be used in the Applicants' suspension copolymerization process or in any polymerization process such as those described in the references above. Still further, other uses for the acid salt or the neutralized BMAP monomer of the present invention will be readily apparent to those of ordinary skill in the art.

For use in the Applicants' copolymerization process, the aqueous BMAP acid salt must be converted back to the BMAP free base. Conversion to free base can be accomplished by adding a suitable neutralizing aqueous base such as ammonia or sodium hydroxide to the solution, preferably ammonia. Addition of this aqueous base results in a suspension from which BMAP free base may be extracted with a substantially water insoluble solvent such as dichloromethane or styrene, preferably styrene.

Most preferably, a styrene or a substituted styrene derivative such as ethylstyrene is used as this extraction solvent and it is desirable then to add to the resultant BMAP/styrene solution the other ingredients comprising the organic phase for the suspension copolymerization process described above. The copolymerization then proceeds as also described previously. Thus, use of a styrene derivative as the extractant is exceedingly practical as a manufacturing step since it eliminates any drying or other secondary recovery step.

A second manner of isolating BMAP acid salt is by recovering it as a solid precipitate. The crude BMAP monomer, perhaps still dissolved in the organic solvent from its preparation, is subjected to a substantially anhydrous mineral acid such as gaseous hydrogen chloride, hydrogen bromide, p-toluenesulfonic acid, methanesulfonic acid or combination of these acids dissolved in a convenient solvent, for example acetic acid. When the crude BMAP monomer free base solution is subjected to this substantially anhydrous acid, solid and purified BMAP acid salt is formed which may be removed from solution by any of the means well known in the art, such as filtration or centrifugation. This BMAP solid salt is substantially pure in the sense that it is free from the non-salt forming compounds present in the original reaction solution. Typically the BMAP solid salt is greater than 90% pure. The salt may then be repeatedly handled and stored for extended periods pending later use in Applicants' copolymerization, or other polymerizations such as those of the above references, or other manners apparent to those ordinarily skilled in the art. It may also be further purified if desired using any conventional means for recrystallization, for example re-dissolution and precipitation using conventional materials.

When it is later desired to use the BMAP solid salt in Applicants' suspension copolymerization, it must first be converted to BMAP free base. Conversion may be done as described above by neutralization with a suitable aqueous base followed by extraction of the neutralized BMAP monomer with a substantially water insoluble solvent, such as dichloromethane or styrene. As also described above, when styrene is used as the extraction solvent the other reactants necessary for the suspension copolymerization may then be added directly to the separated styrene phase for subsequent reaction.

Examples 6–8 are representative of the preparation and isolation of the Applicants' BMAP acid salts as solids. Examples 9–12 similarly describe the purification of this BMAP monomer by forming aqueous solutions of its acid salts after its initial formation. Example 13 describes what is presently considered the most preferred embodiment, involving formation of the hydrochloric acid salt of BMAP in water to extract and purify the BMAP monomer followed by storing this BMAP monomer hydrochloride solution if desired, recovering the free base monomer from the acid solution by treatment with strong base and, simultaneously, extracting the BMAP monomer into sytrene solution which is then reacted to form the preferred polymer-supported 4-(N-benzyl-N-methylamino)pyridine catalysts after adding divinylbenzene, initiator, water, and a suspending agent.

Example 14 describes a study comparing the stability of unpurified BMAP monomer free base and BMAP acid salts prepared according to the present invention. The acid salts were shown to be significantly more stable to storage. After eight days storage at $-5°$ C. the unpurified BMAP monomer formed a residue substantially comprising the spontaneous polymerization product of the monomer, representing 12% of the original monomer. In contrast, a hydrochloric acid salt solution of the BMAP monomer formed polymeric residue representing only 5% of the original BMAP monomer after eight days storage at $3°$ C. Solid BMAP hydrochloride stored at ambient temperature for four weeks formed polymeric residue representing less than 1% of the original monomer. Decreased temperatures do not adversely affect the stability of the solid salt.

Reference will now be made to specific examples for the purpose of further describing and understanding the features of Applicants' preferred embodiments as well as their advantages and improvements over the art. In this regard, where possible, specific reference has been made in the Examples to known prior art processes in order to better understand and distinguish Applicants' invention herein. It is further understood that these Examples are representative only, and that such additional embodiments and improvements of the same are within the contemplation and scope of Applicants' invention as would occur to someone of ordinary skill in this art.

EXAMPLE 1

Suspension Copolymerization Procedure

The following is the procedure used by the applicants in preparing the polymer-supported BMAP catalyst materials according to the previously described embodiments of the invention:

An aqueous phase was first prepared using water and one of the cellulose ether derivatives listed in Example 2, as the stabilizing or suspending agent. 150ml of this aqueous phase was added to a 300 ml round-bottom flask fitted with a condenser, nitrogen purge ports, a thermometer and a stirrer equipped with a glass stirring shaft and Teflon blade. The aqueous solution was purged with nitrogen, stirred and brought to the appropriate reaction temperature to permit free radical generation by the catalyst being used (with Vazo 52, this was about 55° C.). Approximately 30 g of one of the organic monomer phases also listed in Example 2 was then added to the stirred aqueous phase below the liquid surface through a long-necked funnel. The resulting dispersion was maintained at the reaction temperature (about 55° C.) with continued stirring and nitrogen purge for 3 hours until the copolymerization was substantially complete. The dispersion was then heated to about 85° C. and maintained at that temperature for 16 hours with continued stirring and nitrogen purge to finish off the reaction, followed by cooling to room temperature. The insoluble cross-linked polymer-supported BMAP resin beads were removed from the remaining liquid by filtration, rinsed and dried, then their identification and composition confirmed through infrared (I.R.) and elemental combustion analysis.

EXAMPLE 2

Aqueous and Organic Phase Preparations

For use in the procedure of Example 1, aqueous phase solutions were prepared in accordance with the invention using each of the cellulose ether derivatives previously identified in the specification as the stabilizing or suspending agent. These included methylcellulose (such as Methocel A from Dow Chemical Corporation of Midland, Mich. and Culminal from Aqualon Company of Wilmington, Del.); hydroxyethylcellulose (such as Natrosol 250 from Aqualon and Cellosize from Union Carbide Corporation of Danbury, Conn.); hydroxypropylcellulose (such as Klucel J from Aqualon); hydroxypropyl methylcellulose (such as Methocel E, F, J and K and 50-123 from Dow Chemical and Culminal MHPC from Aqualon); hydroxyethyl methylcellulose (such as Culminal from Aqualon); carboxymethyl methylcellulose (such as CMMC from Aqualon); hydrophobically-modified hydroxyethylcellulose (such as HMHEC WSP-M 1017 from Aqualon); carboxymethyl hydroxyethylcellulose (such as CMHEC 37L from Aqualon); and hydroxypropyl hydroxyethylcellulose (such as Natrovis from Aqualon). The aqueous solutions were prepared according to the manufacturer's directions, and generally involved dispersing appropriate amounts of the additive in water at about 85° C. followed by cooling to room temperature to effect proper hydration.

Organic phases for use in the procedure of Example 1 were also prepared in accordance with the invention with varying concentrations of vinyl-substituted BMAP monomer, with styrene itself as the styrenic monomer of choice, and with 55% DVB and Vazo 52 as the cross-linking agent and copolymerization catalyst. BMAP loading was varied at about 15%, about 20%, about 34% and about 50% by weight of the BMAP monomer compared to the total monomer component in the organic phase. This is approximately equivalent to a range of about 7.8 mol%, about 11 mol%, about 20 mol%, and about 33 mol% and to a range of molar ratio of about 1:11, about 1:8. about 1:4 and about 1:2 of BMAP monomer to total monomer present. For example, approximately 30 g of organic phase at 2% cross-linking and 34% BMAP loading contained 11.2 g BMAP monomer, 1.18 g 55% DVB, 19.88 g styrene and 0.16 g Vazo 52. A similarly 4% cross-linked material at 15% BMAP loading contained 3.73 g BMAP monomer, 1.82 g DVB, 18.93 g styrene and 0.12 g Vazo 52, at 20% BMAP loading contained 8.26 g BMAP monomer, 2.74 g DVB, 29.14 g styrene and 0.16 g Vazo 52, and at 50% BMAP loading contained 15.00 g BMAP monomer, 2.20 g DVB, 13.91 g styrene and 0.16 g Vazo 52. By way of further example, 30 g of organic phase at 4% cross-linking and 34% BMAP loading contained 11.2 g BMAP monomer, 2.37 g 55% DVB, 18 94 g styrene and 0 16 g Vazo 52. Still further organic phases were prepared at these four levels of BMAP loading with varying amounts of DVB to prepare copolymer products at levels of cross-linking increasing by 2% up to 12% by weight of the organic phase These additional mixtures were prepared according to known procedures, but simply with stoichiometrically varying amounts of individual components to arrive at the concentrations desired.

EXAMPLE 3

Polymer-Supported BMAP Catalyst

Employing the suspension copolymerization procedure of Example 1 and the aqueous and organic phases of Example 2, the applicants prepared, isolated and identified by I.R. and elemental combustion analysis the polymer-supported BMAP materials obtained from these reactions in accordance with the present invention. In each case, the copolymer yield was well in excess of 90% by weight of the total reactants and was characterized by a predominant and generally smooth and spherical bead form and substantially uniform size ranging from up to about 1.0 mm in diameter with a minimal deviation in bead size in each yield. Each copolymer product was further characterized by the absence of clumping or any significant extraneous material such as the granular powders, flake and other irregular-shaped particles common to literature preparations. Still further, the bead form of each product was hard, durable and generally translucent giving the overall appearance of an effective gel resin for catalytic purposes. Microscopic examination of the copolymers showed no fractures or bubbles in the particle beads as formed. In subsequent testing repeated swellings in a toluene solvent and by stirring in a toluene slurry for more than 2 days, no significant fracturing of the recovered beads was found thereby confirming their durability and recyclability in a commercial setting.

Although preferences as to cross-linking, BMAP loading, the selection of the preferred stabilizing additive and the like will vary in practice depending on many factors, not the least of which is the particular catalytic reaction of interest, certain preferences have been identified at least under the procedures and reactions investigated to date. In this regard, the stabilizing additives most preferred have been Methocel 50-123, HMHEC and CMHEC 37L as previously described. The polymer-supported BMAP resins most preferred have similarly possessed a 34% BMAP loading with either 2% or 4% cross-linking.

EXAMPLE 4

Comparison of 15% Cross-Linked Gel & Macroreticular Resins

Initially, an aqueous phase was prepared by heating 50 ml of water to about 85° C. in an appropriate vessel. With brisk stirring, 0.30 g of Methocel 50-123 was added and the mixture was stirred for about 5 minutes. 150 ml of cold water was added and the mixture was then cooled to room temperature with periodic stirring for about another hour to complete solvation of the stabilizing agent.

Two organic monomer mixtures were prepared using the following recipes: For the gel resin, 10.20 g BMAP monomer (as used in Example 2), 11.62 g styrene, 8.18 g 55% DVB and 0.15 g Vazo 52 were combined with stirring to give a homogeneous solution which was maintained at about 5° C. until its addition to the aqueous phase during copolymerization. For the macroreticular resin, the same procedure was followed using 10.2 g BMAP monomer, 11.62 g styrene; 8.18 g 55% DVB, 9.90 g VMP Naphtha and 0.16 g Vazo 52.

The suspension copolymerization of each monomer phase was then carried out according to the procedure of Example 1. Confirmation of each copolymer composition was by I.R. and elemental combustion analysis. The gel resin appeared as translucent, generally spherical and smooth beads that were consistent with the overall physical properties of the other material described in the specification in accordance with the invention. The macroreticular resin similarly appeared as generally spherical and smooth bead particles also of a substantially uniform size and appearance, but with a whitish color consistent with the presence of substantial microporous channels throughout the bead structure characteristic of such materials. Porosity was confirmed by surface area measurements (ca. 30 m$^2$/g). Both polymer resins proved hard an durable when used in the following reactions and were then recovered for recycling in each case after washing with appropriate solvents to displace any residual water present.

Ester Rearrangement Study

For the purpose of testing and comparing the catalytic effectiveness of these 15% cross-linked gel and macroreticular resins, a dimedone rearrangement reaction was studied in which 3-isobutyryloxy-5,5-dimethyl-2-cyclohexenone was converted to 2-isobutyryl-5,5- dimethyl-1,3-cyclohexanedione. A stock solution of 21.03 g (0.1 mol) 3-isobutyryloxy-5,5-dimethyl-2-cyclohexenone with toluene was then prepared and filled to the line in a 100 ml volumetric flask. A 10 ml aliquot of the solution was pipetted into the test tube containing a 1:1 gram equivalent amount of either the gel or macroreticular resin catalyst prepared in the first part of this Example. The tube was placed in a constant-temperature bath at 100° C., and the reaction mixture was magnetically stirred for 25 hours with samples taken at various times. The gas chromatographic (GC) conditions were set at 12 m DBI @160° C. After the last sample was taken, the reaction mixture was left to filter for 2 hours and weighed. From the GC assay, the percent conversion based on the amount of starting material remaining was then calculated.

For the 15% cross-linked macroreticular resin catalyst, 75.7% conversion was detected after 4 hours and 97.5% conversion after 24 hours in the heated water bath. For the 15% cross-linked gel material, 79.7% conversion occurred after 4 hours and 98.0% conversion after 24 hours of reaction. Similar testing and calculations were then made using homogeneous DMAP material. A comparison was made by dividing the percent conversion for the polymer-supported BMAP material by the corresponding conversion using DMAP multiplied by 100 to convert to a percentage. This percent conversion comparison relative to DMAP for both the macroreticular and the gel resins was 79.0 and 83.2, respectively, after 4 hours and was 98.3 and 99.3%, respectively, after 24 hours. In each case, this reflects a effective result demonstrating the significant catalytic activity of the polymer-supported BMAP material prepared in accordance with the invention relative to the known DMAP standard.

Acetylation of 1-Methylcyclohexanol Study

For the further purpose of testing and comparing the catalytic utility of these 15% cross-linked materials, a procedure similar to the ester rearrangement was used for the acetylation of 1-methylcyclohexanol. A stock solution was first prepared with 30 ml triethylamine (TEA) and 20 ml 1-methylcyclohexanol pipetted into a 200 ml volumetric flask which was filled to the line with toluene. The polymer-supported BMAP catalyst (0.41 mmol, 5 mol%) was added to the culture tube and 10 ml of the stock solution which contained 1 ml (8.1 mmol) 1-methylcyclohexanol and 1.5 ml TEA (10.8 mmol) was also pipetted into the tube. After stirring 10 minutes in a 60° C. constant-temperature bath, 1.5 ml acetic anhydride (15.8 mmol) was added to the tube. Stirring at 60° C. was continued and at various times, samples were taken for determining conversions. After 24 hours, the tube was removed from the hot chloroform bath, and the catalyst was washed with toluene, filtered off and dried for 2 hours. Visual inspection of both the gel and macroreticular resins showed that the beads had held up well during the reaction, with any deterioration evident being the result of the stirring method used in the experiment. It is understood that alternative stirring techniques such as used in Example 1 will eliminate catalyst breakage due to this cause.

Following GC analysis of the samples, it was determined that for the 15% cross-linked macroreticular resin, 21.6% conversion to the acetate occurred after 6 hours while 37.1% was converted after 24 hours in the bath. For the 15% cross-linked gel resin, the corresponding values were 25.4% conversion after 6 hours and 38.1% conversion after 24 hours. These conversions were then compared relative to similar DMAP-catalyzed reactions with the percent conversion relative to DMAP for the macroreticular resin being 27.1% after 6 hours and 38.4% after 24 hours, and for the gel resin being 31.9% and 39.4%, respectively. As with the ester rearrangement, this testing confirmed the effective catalytic activity of both the gel and macroreticular resins prepared according to the applicants' invention. This was true even with the high 15% cross linking in these resins which is substantially greater than may be desired under the circumstances of a particular reaction. As this cross-linking decreases, activity levels would increase both in absolute terms and relative to similar DMAP conversions.

EXAMPLE 5

Comparison of Aqueous Phases

Suspension copolymerizations were carried out in the manner described as follows comparing one of the preferred aqueous phases in the invention using Methocel 50-123 as the stabilizing additive against the aqueous phases reported by groups led by Tomoi (Tomoi, M., and Ford, W. T., *J. Am. Chem. Soc.*, 103, 3828 (1981)), and Fréchet (Deratini, A., Darling, G. D., Horak, D., and Fréchet, J. M. J., *Macromolecules*, 20, 767 (1987)) and comparing the preferred organic phase in the invention against the alternative recommended by Fréchet (Deratini, A., Darling, G. D., Horak, D., and Fréchet, J. M. J., *Macromolecules*. 20, 767 (1987)).

Preparation of Aqueous Phases

The Tomoi aqueous phase was prepared by mixing a solution containing 1.35 g gelatin, 12.5 g Merquat 100 (which is poly(diallyldimethylammonium chloride) marketed by Calgon Corp., Pittsburg, Pa.) and 5.1 g boric acid in 450 g of water. Its PH was adjusted to 10.0 with a 25% aqueous solution of sodium hydroxide.

The Fréchet aqueous phase was prepared by simply dissolving 6.75 g polyvinylalcohol (Airvol 523 manufactured by Air Products and Chemicals, Inc. of Allentown, Pa.) in 450 g of water.

The aqueous phase in accordance with the present invention which was in this test was prepared as described in Example 4.

Preparation of Organic Phases:

Two organic phases were prepared for use in the comparison. The first involved subsequent attachment of 4-(N-methylamino)pyridine groups to a preformed cross-linked chloromethylated polystyrene. This procedure was preferred by Fréchet and the initial organic phase was prepared as a solution containing 23.75 g styrene, 8.35 g chloromethylstyrene, 2.4 g 55% DVB and 0.1 g Vazo 52, which was maintained between about 0°-10° C. before copolymerization. The second procedure preferred by the applicants involved direct copolymerization of a comonomer solution of styrene and the vinyl-substituted BMAP monomer. This required preparing a solution containing 11.2 9 of the BMAP mononer, 18.94 g styrene, 2.37 g 55% DVB and 0.16 g Vazo 52 according to Example 2 which was also maintained between about 0°-10° C. before copolymerization.

Copolymerization and Results

The copolymerization reactions in this Example were carried out using the same procedure and amounts as in Example 1. Following cooling and removal of the insoluble product by filtration, the following results were observed:

The cross-linked copolymers prepared using the Tomoi aqueous phase and both organic phases yielded particles that were not uniformly spherical and varied greatly in size. The products contained a significant amount of flake and fine powders, making it very difficult to filter or recover from any commercial process. The distorted beads showed visible signs of fractures under microscopic analysis and readily broke into smaller fragments upon swelling and recapture from a toluene solvent. Similarly, severe fracturing was noted when a slurry of this material in toluene was stirred for several hours.

The cross-linked copolymers prepared using the Fréchet aqueous phase and both organic phases consisted substantially of clumps of small distorted bead forms. Attempts to separate these particles resulted in substantial fracture of the discernable beads present in the material. Microscopic examination of these bead clumps revealed both fractures and many tiny bubbles and other imperfections in the particles. Similar to the Tomoi material, these copolymers also broke into smaller fragments upon repeated swelling in toluene and upon stirring in a slurry for several hours.

The cross-linked copolymers prepared using the aqueous phase of the present invention (with both organic phases) produced materials in yields over 90% by weight consisting primarily of smooth spherical beads that were hard and translucent giving all appearances of a superior gel resin structure. The beads were substantially uniform in size with minimal deviation of about 10% from the median or average bead size in each case. Little or no extraneous irregular-shaped material was produced, and microscopic examination showed no signs of fractures or bubbles in the produced particles. Of equal importance, neither repeated swelling in toluene nor nondestructive stirring in a toluene slurry for more than two days resulted in any significant fracturing of the beads thereby confirming their durability for recycling in many acylation, alkylation and other related reactions of commercial significance.

EXAMPLE 6

Preparation of the Hydrobromide Salt of Vinyl-Substituted BMAP Monomer (N-vinylbenzyl-N-methyl-4-pyridylamine hydrobromide)

To a dry, nitrogen-purged round-bottom flask is charged 4-(N-methylamino)pyridine (43.26 g), sodium hydride (80 wt. % in mineral oil, 14.9 g), and anhydrous tetrahydrofuran (250 mL). After 2.5 hr, vinylbenzyl chloride (a mixture of about 60 wt. % 3-vinylbenzyl chloride and about 40 wt. % 4-vinyl benzyl chloride, according to the manufacturer) is added. The temperature is maintained below 40° C. for 4 hr. Excess sodium hydride is destroyed by addition of water. After filtration of insoluble salts, a solution of 30 wt. % hydrogen bromide in acetic acid (80.1 mL) is added with stirring while the temperature is maintained below 30° C. After 15 minutes the hydrobromide salt of BMAP monomer is isolated as a solid by filtration. The solid is further purified by dissolving in 800 mL of dichloromethane, then precipitated by the addition of 800 mL of tetrahydrofuran, to yield 52.6 g (43%) of N-vinylbenzyl-N-methyl-4-pyridylamine hydrobromide as a crystalline solid, m.p. 169°–171° C. The structure and composition were confirmed by NMR and elemental combustion analysis. This material was stable to storage and could be converted by treatment with base to BMAP monomer which was suitable for copolymerization as described above.

EXAMPLE 7

Preparation of the Hydrochloride Salt of BMAP Monomer (N-vinylbenzyl-N-methyl-4-pyridylamine hydrochloride)

Using the method of Example 6 but substituting hydrogen chloride for hydrogen bromide gave 72% of N-vinylbenzyl-N-methyl-4-pyridylamine hydrochloride, m.p. 173°–175° C. The structure and composition were confirmed by NMR, combustion elemental analysis and silver nitrate titration.

EXAMPLE 8

Preparation of the p-toluenesulfonate Salt of BMAP Monomer (N-vinylbenzyl-N-methyl-4-pyridylamine p-toluenesulfonate)

Using the method of Example 6 but substituting p-toluenesulfonic acid hydrate for hydrogen bromide gave 50% of N-vinylbenzyl-N-methyl-4-pyridylamine p-toluenesulfonate, m.p. 129°–131.5° C. The proposed structure was confirmed by NMR and IR.

EXAMPLE 9

Preparation of the Methanesulfonate Salt of BMAP Monomer as an Aqueous Solution, and Conversion of it to Free BMAP Monomer To a dry, nitrogen-purged round-bottom flask was charged 4-(N-methylamino)pyridine (4.33 g), sodium hydride (80 wt. % in mineral oil, 1.5 g), and 25 mL of anhydrous tetrahydrofuran. After 2.5 hr of agitation, hydrogen evolution ceased and toluene (60 ml) was introduced. The tetrahydrofuran was removed by distillation. Vinylbenzyl chloride (a mixture of 3- and 4-vinylbenzyl chloride, 6.36 g) was added, and the temperature was kept below 40° C. for 4 hr. Excess sodium hydride was quenched by addition of water. Sodium chloride was removed by filtration. Aqueous 50 wt. % methanesulfonic acid (23 g) was added to the toluene solution while keeping the temperature below 40° C. Two layers were formed. The aqueous layer contained N-vinylbenzyl-N-methyl-4-pyridylamine methanesulfonate was separated from the toluene layer. The remaining toluene layer contained mineral oil, some unreacted vinylbenzyl chloride, and other impurities, and was discarded. Aqueous ammonia (28 wt. %) was then added to the acid solution of BMAP monomer methanesulfonate until the pH reached 9.2. The resulting suspension was extracted with dichloromethane, the extract dried over magnesium sulfate, and evaporated to yield the BMAP monomer free base as a clear, viscous brown oil which solidified on standing. The NMR and IR spectra were identical with those of a purified sample of BMAP monomer free base. The monomer was suitable for copolymerization with styrene and divinylbenzene, in the manner described in Examples 1 through 5.

EXAMPLE 10

Preparation of the Sulfate Salt of BMAP Monomer as an Aqueous Solution, and Conversion of it to Free BMAP Monomer The process of Example 9 was repeated, except that sulfuric acid (20 mL of 6M) was substituted for the aqueous methanesulfonic acid. BMAP monomer (7.91 g, 88% yield) was obtained, and was found to be 94.6% pure by gas chromatography.

EXAMPLE 11

Preparation of the Formate Salt of BMAP Monomer as an Aqueous Solution, and Conversion of it to Free BMAP Monomer The process of Example 9 was repeated, except that 90 wt. % formic acid (5.1 mL) was substituted for the aqueous ethanesulfonic acid. BMAP monomer was obtained in 86% yield and was 95.8% pure by gas chromatography.

EXAMPLE 12

Preparation of the Phosphate Salt of BMAP Monomer as an Aqueous Solution, and Conversion of it to Free BMAP Monomer The process of Example 9 was repeated, except that 85 wt. % phosphoric acid (8.2 mL) was substituted for the aqueous methanesulfonic acid. BMAP monomer was obtained in 92.3% yield and was 96% pure by gas chromatography.

EXAMPLE 13

Preparation of Polymer-Supported 4-(N-benzyl-N-methylamino) pyridine Catalysts To a dry, nitrogen-purged round-bottom flask was charged 4-(N-methylamino)pyridine (43.26 g), sodium hydride (80 wt. % in oil, 14.9 g), and anhydrous tetrahydrofuran (250 mL). After hydrogen evolution ceased, toluene (600 mL) was added and most of the tetrahydrofuran was removed by distillation. A mixture of 3- and 4-vinylbenzyl chloride (commercial vinylbenzyl chloride, 63.6 g) was added. The temperature was maintained below 40° C. for 6 hr. Excess sodium hydride was quenched with water and carbon dioxide. Sodium chloride was separated by filtration.

To the filtrate was added 18 wt. % hydrochloric acid (115 mL) while maintaining the temperature below 40° C. The aqueous layer, containing the BMAP monomer hydrochloride, was separated and washed with toluene. Aqueous ammonia (28 wt. %) was added to the aqueous layer until the pH was 9.0. Styrene (141.2 g) was added and the aqueous layer was separated and discarded. The toluene solution was washed once with water. The resulting toluene solution is found to contain 34.5 wt. % of BMAP monomer by titration with perchloric acid in acetic acid. To a portion (217.9 g) of the styrene solution was added 17.1 g of 55 wt. % divinylbenzene and 1.17 g of Vazo 52 (2,2'-azobis(2,4-dimethylvaleronitrile) while keeping the mixture at room temperature.

An aqueous phase was prepared by dispersing 0.8 g of Methocel 50-123 with stirring in 800 mL of water heated to 85° C., followed by cooling the dispersion to 25° C. for 30 minutes. This aqueous suspension was heated to 58° C., stirred, and agitated. The styrene - BMAP monomer - divinylbenzene - Vazo solution was then added below the liquid surface to the stirred aqueous phase. The resulting dispersion was maintained at 58° C. for 3 hours, maintaining the nitrogen purge and agitation. The mixture was then heated at about 65° C. for 16 hours. The dispersion was cooled and filtered to yield 219 g of highly spherical beads of polymer-supported 4-(N-benzyl-N-methylamino) pyridine found to have useful catalytic activity.

EXAMPLE 14

Comparative Stability of BMAP Free Base and BMAP Hydrochloride Salts

Stability of the BMAP free base 26.1 g BMAP monomer was prepared by the Tomoi method as a toluene solution. Toluene was removed at reduced pressure to give the BMAP monomer free base as a dark viscous oil which was placed in a glass bottle and stored in a freezer at −5° C. eight days. The resulting monomer was stirred with excess cyclohexane and a residue, substantially representing the spontaneous polymerization of the monomer, formed. The monomer solution was decanted and the remaining residue washed with two more portions of cyclohexane. After drying, the polymeric residue (3.2 g) was found to represent 12% of the original mononer portion.

Stability of the BMAP acid salt solution 25.3 g BMAP mononer in the free base form was prepared as described above to which 200 ml of aqueous hydrochloric acid (5%) was added. The resulting solution was placed in a glass bottle and stored in a refrigerator at 3° C for eight days. The solution was treated with a slight excess of sodium hydroxide and the resulting three phase mixture extracted with cyclohexane to dissolve the BMAP monomer. The organic and aqueous layers were removed by decantation and the remaining polymeric residue washed with two additional portions of cyclohexane and dried. The residue, 1.3 g substantially comprising the spontaneous polymerization product of the monomer, represented 5% of the original monomer portion.

Stability of the solid BMAP acid salt 30.0 g of the solid BMAP hydrochloride salt prepared as in Example 7 was stored in a glass bottle at room temperature for four weeks. The resulting white solid appeared unchanged. The BMAP hydrochloride salt was dissolved in 200 ml water and the resulting solution treated with 150 ml aqueous sodium hydroxide (5 %). Only a trace of residue (0.2 g) resulted, substantially comprising the spontaneous polymerization product of the monomer, representing less than 1% of the original monomer portion.

What is claimed is:

1. A process for preparing a polymer having substituted aminopyridine groups comprising neutralizing a vinyl-substituted 4-(N-benzyl-N-methylamino)pyridine acid salt with a suitable base followed by polymerization of an organic phase containing the resultant free base monomer.

2. The process of claim 1 and further comprising isolating the neutralized vinyl-substituted 4-(N-benzyl-N-methylamino)pyridine monomer free base prior to the polymerization.

3. The process of claim 1 in which the vinyl-substituted 4-(N-benzyl-N-methylamino)pyridine is N-(3-vinylbenzyl)-N-methyl-4-aminopyridine or N-(4-vinylbenzyl)-N-methyl-4-aminopyridine or a mixture thereof.

4. The process of claim 1 in which the base is aqueous.

5. The process of claim 2 in which the base is selected from the group consisting of:
ammonia; and
sodium hydroxide.

6. The process of claim 1 in which the vinyl-substituted 4-(N-benzyl-N-methylamino)pyridine acid salt is an aqueous salt solution.

7. The process of claim 1 in which said isolating is by extraction with a substantially water insoluble solvent.

8. The process of claim 7 in which the solvent is selected from the group consisting of:
styrene; and
dichloromethane.

9. The process of claim 1 in which said process is a suspension copolymerization for preparing in high yield a catalytic polymer in the presence of an aqueous phase containing a cellulose ether derivative as the stabilizing agent and further in which the organic phase contains a suitable cross-linking agent and a free radical-generating catalyst.

10. The process of claim 9 in which the cross-linking agent is divinylbenzene.

11. The process of claim 9 in which the cellulose ether derivative is selected from the group consisting of:
methylcellulose;
hydroxyethylcellulose;
hydroxypropylcellulose;
hydroxypropyl methylcellulose;
hydroxyethyl methylcellulose;
carboxymethyl methylcellulose;
hydrophobically-modified hydroxyethylcellulose;
carboxymethyl hydroxyethylcellulose; and
hydroxypropyl hydroxyethylcellulose.

12. A process for preparing in high yield a catalytic polymer having substituted aminopyridine groups comprising the steps of:
   a. preparing a vinyl-substituted 4-(N-benzyl-N-methylamino)pyridine monomer in a substantially water insoluble solvent;
   b. extracting the monomer with an aqueous acid sufficiently strong to form a salt with the monomer.
   c. neutralizing the resultant monomer acid salt with a suitable base; and
   d. separating the resultant monomer free base by extraction with a second substantially water insoluble solvent followed by the suspension copolymerization of an organic phase containing the monomer free base, a styrene monomer and a suitable cross-linking agent and free radical-generating catalyst in the presence of an aqueous phase containing a cellulose ether derivative as the stabilizing agent.

13. The process of claim 12 in which the vinyl-substituted 4-(N-benzyl-N-methylamino)pyridine is N-(3-vinylbenzyl)-N-methyl-4-aminopyridine or N-(4-vinylbenzyl)-N-methyl-4-aminopyridine.

14. The process of claim 12 in which the acid is hydrochloric acid.

15. The process of claim 12 in which the base is aqueous.

16. The process of claim 15 in which the base is sodium hydroxide.

17. The process of claim 12 in which the second substantially water insoluble solvent is a monomer for copolymerization with said vinyl-substituted 4-(N-benzyl-N-methylamino)pyridine.

18. The process of claim 17 in which the second solvent is styrene.

19. The process of claim 12 in which the cross-linking agent is divinylbenzene.

20. The process of claim 12 in which the cellulose ether derivative is selected from the group consisting of:
methylcellulose;
hydroxyethylcellulose;
hydroxypropylcellulose;
hydroxypropyl methylcellulose;
hydroxyethyl methylcellulose;
carboxymethyl methylcellulose;
hydrophobically-modified hydroxyethylcellulose;
carboxymethyl hydroxyethylcellulose; and
hydroxypropyl hydroxyethylcellulose.

* * * * *